(12) United States Patent
Thakur et al.

(10) Patent No.: US 10,835,129 B2
(45) Date of Patent: Nov. 17, 2020

(54) SYSTEM TO DIAGNOSE AND MANAGE ORTHOSTATIC INTOLERANCE

(71) Applicant: Cardiac Pacemakers, Inc., St. Paul, MN (US)

(72) Inventors: Pramodsingh Hirasingh Thakur, Woodbury, MN (US); David J. Ternes, Roseville, MN (US); Amy Jean Brisden, Saint Paul, MN (US); Qi An, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 264 days.

(21) Appl. No.: 15/696,911

(22) Filed: Sep. 6, 2017

(65) Prior Publication Data

US 2018/0064350 A1 Mar. 8, 2018

Related U.S. Application Data

(60) Provisional application No. 62/383,805, filed on Sep. 6, 2016.

(51) Int. Cl.
*A61B 5/0205* (2006.01)
*A61N 1/365* (2006.01)
(Continued)

(52) U.S. Cl.
CPC .......... *A61B 5/0205* (2013.01); *A61B 5/0215* (2013.01); *A61B 5/1116* (2013.01);
(Continued)

(58) Field of Classification Search
CPC .................................................. A61B 5/0205
See application file for complete search history.

(56) References Cited

U.S. PATENT DOCUMENTS 6,719,701 B2   4/2004   Lade
8,343,049 B2 * 1/2013   Hatlestad ........... A61B 5/02405
                                                600/301
(Continued)

FOREIGN PATENT DOCUMENTS

WO    WO-9826716 A1    6/1998
WO    WO-2004095306 A1  11/2004
(Continued)

OTHER PUBLICATIONS

"Tilt Table Testing", Children's Heart Specialists; http://mykentuckyheart.com/services/tilt-table-testing.html, (2008-2016), 2.

(Continued)

*Primary Examiner* — Alyssa M Alter
(74) *Attorney, Agent, or Firm* — Schwegman Lundberg & Woessner, P.A.

(57) ABSTRACT

An apparatus includes a posture sensing circuit configured to detect a change in posture of a subject; a cardiac signal sensing circuit configured to generate a sensed cardiac signal, wherein the sensed cardiac signal includes heart rate information of the subject; a physiologic sensing circuit configured to generate a sensed physiologic signal, wherein the physiologic signal includes information related to blood pressure of the subject; a storage buffer; and a control circuit operatively coupled to the posture sensing circuit and the storage buffer. The control circuit is configured to initiate storage of the heart rate information and the information related to blood pressure in response to a detected change in posture of the subject.

20 Claims, 3 Drawing Sheets

(51) Int. Cl.
*A61B 5/11* (2006.01)
*A61B 5/0215* (2006.01)
*G08B 21/04* (2006.01)
*A61B 5/00* (2006.01)
*A61B 7/04* (2006.01)
*A61B 5/024* (2006.01)

(52) U.S. Cl.
CPC .......... *A61B 5/686* (2013.01); *A61N 1/36585* (2013.01); *G08B 21/0446* (2013.01); *G08B 21/0453* (2013.01); *A61B 5/0004* (2013.01); *A61B 5/02438* (2013.01); *A61B 5/4035* (2013.01); *A61B 5/4076* (2013.01); *A61B 5/7275* (2013.01); *A61B 5/7289* (2013.01); *A61B 7/04* (2013.01); *A61B 2562/0219* (2013.01)

(56) References Cited

U.S. PATENT DOCUMENTS

| | | |
|---|---|---|
| 2007/0161912 A1 | 7/2007 | Zhang et al. |
| 2008/0011545 A1 | 1/2008 | Turner |
| 2008/0082001 A1 | 4/2008 | Hatlestad et al. |
| 2012/0157799 A1* | 6/2012 | Patangay .............. A61B 5/0031 600/301 |
| 2013/0237863 A1 | 9/2013 | Song et al. |
| 2013/0324868 A1 | 12/2013 | Kaib et al. |
| 2014/0358193 A1* | 12/2014 | Lyons ................ A61N 1/36139 607/48 |

FOREIGN PATENT DOCUMENTS

| | | |
|---|---|---|
| WO | WO-2013022886 A1 | 2/2013 |
| WO | WO-2013069004 A1 | 5/2013 |
| WO | WO-2015084557 A1 | 6/2015 |
| WO | WO-2018048825 A1 | 3/2018 |

OTHER PUBLICATIONS

Arenas, I.A., et al., "Dynamic genetic linkage of intermediate blood pressure phenotypes during postural adaptations in a founder population", Physiol Genomics 45(4), (Feb. 15, 2013), 138-150.

Hongo, Richard H., et al., "Evaluating Patients with Unexplained Syncope", Cardiovasc Rev Rep. 2004; 25(5), (2004), 1-8.

Kusukawa, R., et al., "Hemodynamic determinants of the amplitude of the second heart sound", J. Appl. Physiol (21) 3, (Aug. 30, 1965), 938-946.

Mathias, C.J., et al., "Postural tachycardia syndrome—current experience and concepts", Nat. Rev. Neurol. 8, (2012), 22-34.

"International Application Serial No. PCT/US2017/050160, International Preliminary Report Patentability dated Mar. 21, 2019", 9 pgs.

"International Application Serial No. PCT/US2017/050160, International Search Report dated Dec. 5, 2017", 4 pgs.

"International Application Serial No. PCT/US2017/050160, Written Opinion dated Dec. 5, 2017", 7 pgs.

* cited by examiner

SYSTEM TO DIAGNOSE AND MANAGE ORTHOSTATIC INTOLERANCE

CLAIM OF PRIORITY

This application claims the benefit of priority under 35 U.S.C. § 119(e) of U.S. Provisional Patent Application Ser. No. 62/383,805, filed on Sep. 6, 2016, which is herein incorporated by reference in its entirety.

BACKGROUND

Ambulatory medical devices include implantable medical devices (IMDs), wearable medical devices, handheld medical devices, and other types of medical devices. Some examples of IMDs include cardiac function management (CFM) devices such as implantable pacemakers, implantable cardioverter defibrillators (ICDs), subcutaneous implantable cardioverter defibrillators (S-ICDs), cardiac resynchronization therapy devices (CRTs), and devices that include a combination of such capabilities. The devices can be used to treat patients or subjects using electrical or other therapy, or to aid a physician or caregiver in patient diagnosis through internal monitoring of a patient's condition.

Some implantable medical devices can be diagnostic-only devices, such as implantable loop recorders (ILRs), body-insertable cardiac monitors (ICMs), and subcutaneously implantable heart failure monitors (SubQ HFMs). The devices may include electrodes in communication with one or more sense amplifiers to monitor electrical heart activity within a patient, or can include one or more sensors to monitor one or more other internal patient parameters. Subcutaneously implantable devices may include electrodes that are able to sense cardiac signals without being in direct contact with the patient's heart. Other examples of IMDs include implantable drug delivery systems or implantable devices with neural stimulation capability (e.g., vagus nerve stimulator, baroreflex stimulator, carotid sinus stimulator, spinal cord stimulator, deep brain stimulator, etc.).

Some examples of wearable medical devices include wearable cardioverter defibrillators (WCDs) and wearable diagnostic devices (e.g., an ambulatory monitoring vest, holter monitor, cardiac event monitor, or mobile cardiac telemetry devices). WCDs can be monitoring devices that include surface electrodes. The surface electrodes may be arranged to provide one or both of monitoring to provide surface electrocardiograms (ECGs) and delivery of cardioverter and defibrillator shock therapy. In some examples, a wearable medical device can also include a monitoring patch worn by the patient such as an adherable patch or can be included with an article of clothing worn by the patient.

Some examples of handheld medical devices include personal data assistants (PDAs) and smartphones. The handheld devices can be diagnostic devices that record an electrocardiograph (ECG) or other physiological parameter while the device is resting in the patient's hand or being held to the patient's chest.

CFM devices and diagnostic-only devices can be used to record information related to cardiac events experienced by the patient. These recorded episodes can be uploaded from the medical device and evaluated by a clinician. These recordings can be used to monitor the progression of disease by the patient. Knowledge regarding the onset of a physiological condition can be useful to physicians and clinicians for diagnostic purposes or to tailor performance of a medical device to that patient's needs to provide the most effective patient therapy.

Overview

Ambulatory medical devices can be helpful to monitor patient physiology to correctly detect a patient condition and to track progression of the patient condition. Patient monitoring that is restricted to a clinical setting may not be able to replicate the conditions causing a patient's symptoms, and may not provide all of the information necessary to completely assess the patient's physiological condition.

One example of an ambulatory medical device system of the present subject matter can include a posture sensing circuit, a cardiac signal sensing circuit, a physiological sensing circuit, a storage buffer, and a control circuit. The posture sensing circuit detects a change in posture of a subject. The cardiac signal sensing circuit generates a sensed cardiac signal that includes heart rate information of the subject. The physiologic sensing circuit generates a sensed physiologic signal that includes blood pressure information of the subject. The control circuit initiates storage of the heart rate information and the blood pressure information in response to a detected change in posture of the subject.

This section is intended to provide a brief overview of subject matter of the present patent application. It is not intended to provide an exclusive or exhaustive explanation of the invention. The detailed description is included to provide further information about the present patent application such as a discussion of the dependent claims and the interrelation of the dependent and independent claims in addition to the statements made in this section.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, the various examples discussed in the present document.

DETAILED DESCRIPTION

An ambulatory medical device can include one or more of the features, structures, methods, or combinations thereof described herein. For example, an implantable loop recorder may be implemented to include one or more of the advantageous features or processes described below. It is intended that such a monitor, stimulator, or other ambulatory device need not include all of the features described herein, but may be implemented to include selected features that provide for unique structures or functionality. Such a device may be implemented to provide a variety of therapeutic or diagnostic functions.

Figure 1:
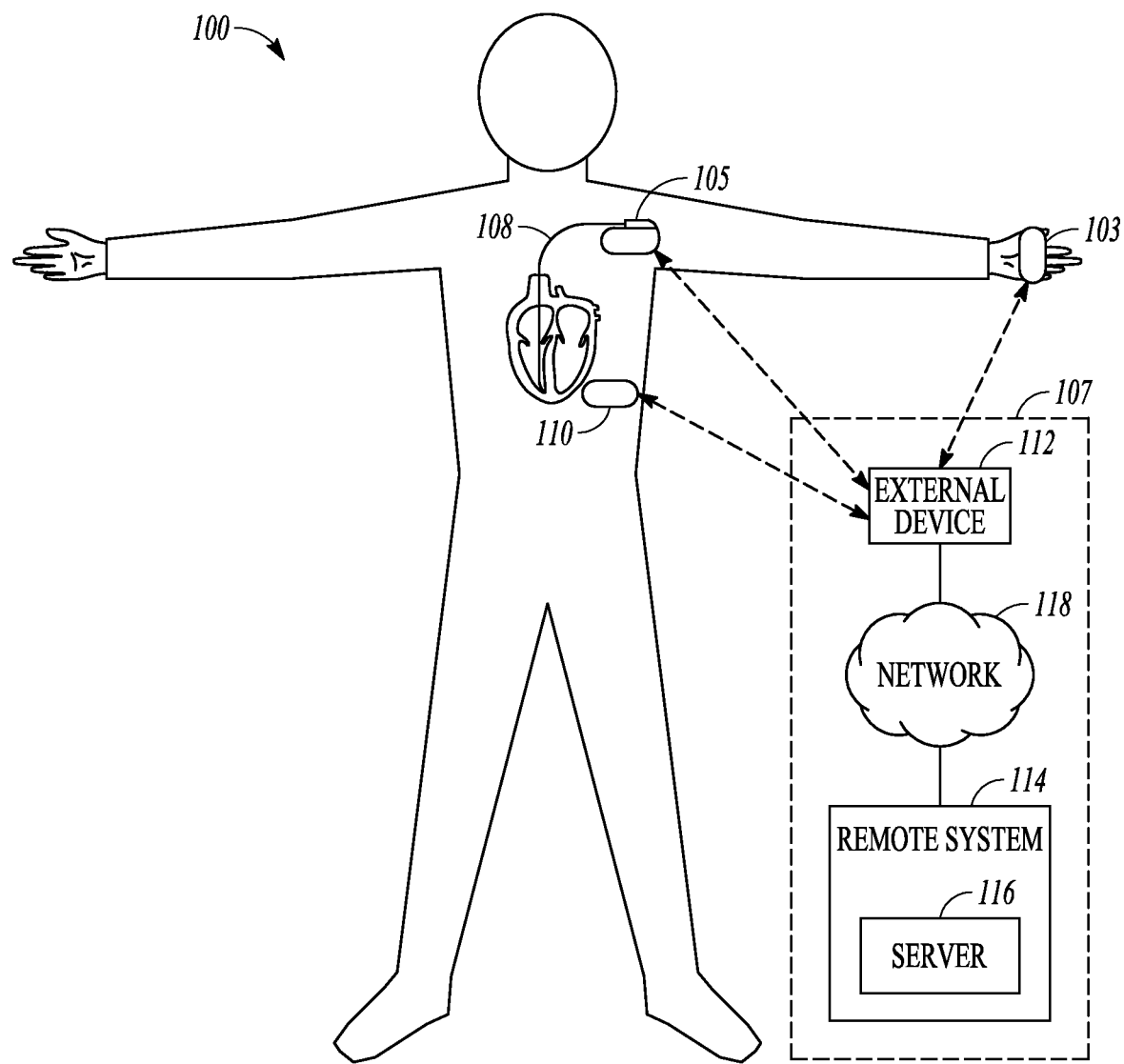
FIG. 1 is an illustration of portions of an example of a medical device system.

FIG. 1 is an illustration of portions of an example of an ambulatory medical device system 100. The system 100 may include one or more ambulatory medical devices, such as an implantable medical device 105, a wearable medical device 110, or a handheld medical device 103. The implantable medical device 105 may be conventionally implantable or subcutaneously implantable. The implantable medical device 105 may be a cardiac function management device designed to provide electrical device based therapy to the subject using electrodes included on a cardiac lead 108, or the implantable medical device may be an implantable loop recorder (ILR), or insertable cardiac monitor (ICM).

One or more of the ambulatory medical devices can include a communication circuit (e.g., a telemetry circuit) to communicate device-determined information to a communication system 107. The communication system 107 can include an external communication device 112 and a remote system 114 that communicates with the external communication device 112 via a network 118 (e.g., the internet, a proprietary computer network, or a cellular phone network). The remote system 114 may include a server 116 remotely located from the external communication device 112 and the subject to perform patient management functions. The external communication device 112 may include a programmer to program therapy parameters of a device-based therapy provided by the implantable medical device, to program diagnostic set-up parameters, or to query data stored in the medical device. One or both of the external communication device 112 and the remote system 114 may include a display to present the information to a user, such as a clinician. If the medical device is handheld or wearable, the display screen may be included in the medical device.

One or more of the ambulatory medical devices can include sense amplifiers operatively coupled to electrodes to produce a sensed electrogram signal representative of cardiac depolarization of the subject. An ambulatory medical device may also include one or more physiologic sensors such as a respiration sensor, blood pressure sensor, a heart sound sensor, a posture sensor, or a physical activity sensor.

Orthostatic response of a patient is the physiologic response to a transition to an upright posture. The transition to an upright posture can be accompanied by a drop in venous system return, which is a drop in the rate of blood flow back to the heart. The decrease in venous system return can cause a reduction in cardiac stroke volume and cause an acute drop in blood pressure. Normally, a person's baroreflex mechanism responds to the drop in blood pressure by increasing heart rate and the blood pressure returns to normal.

However, some patients exhibit orthostatic intolerance (OI) due to an inappropriate baroreflex response. For example, a patient may respond to the upright transition with an increase in hear rate that is too great. This can be referred to as postural orthostatic tachycardia syndrome (POTS). POTS may have adrenergic causes, neuropathic causes, or can be caused by hypovolemia. POTS may be indicated when a patient experiences an abnormally large increase in heart rate when changing from a recumbent positon to an upright position, but the change in position is not accompanied by a drop in blood pressure.

In another example, a patient may have an insufficient heart rate response to the transition and the blood pressure does not increase sufficiently. This can be referred to as orthostatic hypotension OH. OH may be indicated when a patient experiences dizziness, light headedness, or syncope when changing from a recumbent positon to an upright position. The cause of OH can remain unexplained in a significant proportion of patients with OH.

The orthostatic response of a patient may not be static, but may change over time and may be different for different situations of the patient, such as between active and resting for example. Device-based monitoring of the subject can provide advantages over clinical-based orthostatic response analysis. Typically for a clinical assessment, a patient is strapped to a table that can be tilted. The table is then tilted from a supine position to a near vertical position and the patient's response is monitored and the patient's physiological condition assessed.

Tests conducted in a clinical setting may not provide all of the information necessary to completely assess the patient's physiological condition. The clinical setting may not be able to replicate the conditions causing a patient's symptoms. Additionally, clinical testing may not uncover lifestyle influences on the patient's symptoms. This can lead to under-detection and under-diagnosis of orthostatic intolerance. Further, clinical-based monitoring may depend on repeat assessments of the patient in the clinic to detect a change in the patient's orthostatic response. As explained previously herein, some ambulatory medical devices can be used to record signals produced by sensors included in the devices. These recorded signals can provide useful information remote from a clinical setting that can be uploaded and evaluated by a clinician to monitor the patient's physiological condition.

Figure 2:
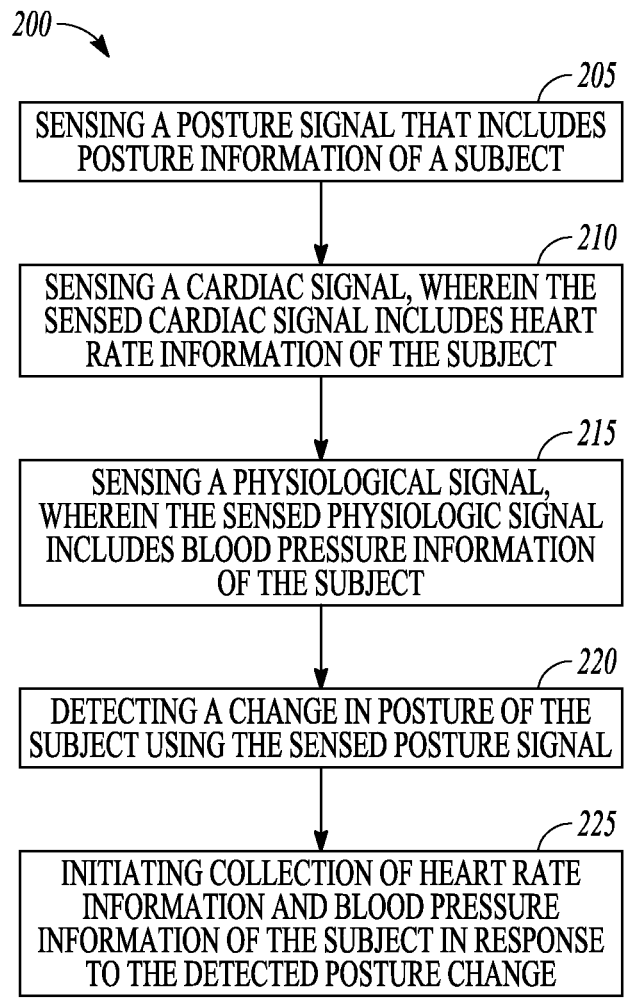
FIG. 2 is a flow diagram of a method of controlling operation of an ambulatory medical device or device system to monitor orthostatic response of a patient or subject.

FIG. 2 is a flow diagram of a method 200 of controlling operation of an ambulatory medical device to monitor orthostatic response of a patient or subject. At 205, a posture signal is sensed. The posture signal includes posture information of the subject. An example of a posture sensor is a three-dimensional direct current (DC) accelerometer. The accelerometer provides a DC-responsive electrical signal output for each of three mutually orthogonal axes. The accelerometer is DC-responsive in that the accelerometer provides an output even when the accelerometer is exposed to acceleration that is not time varying. The outputs of the accelerometer can be compared to specified thresholds to determine the posture of the subject.

At 210, a cardiac signal is sensed. The cardiac signal includes heart rate information of the subject. The cardiac signal can be sensed using electrodes operatively coupled to one or more sense amplifiers to detect cardiac depolarization.

At 215, a physiologic signal is sensed using a physiologic sensor. The sensed physiologic signal includes blood pressure information for the subject. The physiologic sensor may be a blood pressure sensor and the physiologic signal is directly representative of blood pressure of the subject, or the physiologic sensor may be a sensor that provides a signal that is a surrogate for blood pressure information. A surrogate for blood pressure means that information related to blood pressure of the subject can be gleaned from the sensed surrogate signal.

An example of a surrogate sensor for blood pressure is a heart sound sensor. Heart sounds are associated with mechanical vibrations from activity of a patient's heart and the flow of blood through the heart. Heart sounds recur with each cardiac cycle and are separated and classified according to the activity associated with the vibration. The first heart sound (S1) is the vibrational sound made by the heart during tensing of the mitral valve. The second heart sound (S2) marks the beginning of diastole. The third heart sound (S3) and fourth heart sound (S4) are related to filling pressures of the left ventricle during diastole. A heart sound signal produced by a heart sound sensor circuit can be an electrical signal representative of one or more heart sounds. The S2 heart sound can be related to a pressure difference between the aorta and the left ventricle at the time of valve closure.

It follows that S2 heart sound information can provide information related to blood pressure of the subject.

Returning to FIG. 2 at 220, a change in posture of the subject is detected using the sensed posture signal. At 225, heart rate information and blood pressure information of the subject is collected in response to the detected posture change using the cardiac signal and the physiologic signal. The collected information can be used to detect orthostatic intolerance of the patient or subject.

Figure 3:
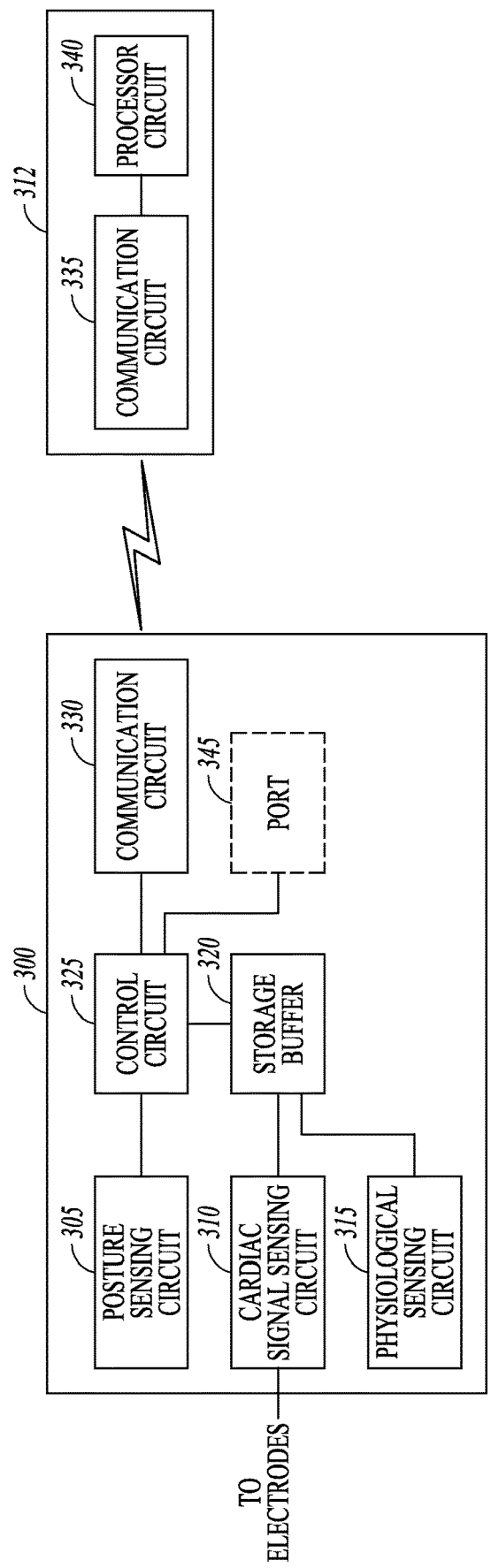
FIG. 3 is a block diagram of portions of an example of an ambulatory medical device.

FIG. 3 is a block diagram of portions of an example of an ambulatory medical device that can be included in an ambulatory medical device system. The device 300 can be an implantable device (e.g., CFM device, ILR, or ICM), or the device can be wearable (e.g., a wearable patch) or handheld. The ambulatory medical device includes a posture sensing circuit 305, a cardiac signal sensing circuit 310, a physiologic sensing circuit, a storage buffer memory 320, and a control circuit 325.

The posture sensing circuit 305 detects a change in posture of a subject. The posture sensing circuit can include a DC accelerometer circuit or a tilt switch circuit. The cardiac signal sensing circuit 310 generates a sensed cardiac signal that includes heart rate information. For instance, the cardiac signal may include R-waves that indicate cardiac depolarization. The physiologic sensing circuit 315 generates a sensed physiologic signal that includes blood pressure information of the subject. In some examples, the physiologic sensing circuit is an implantable blood pressure sensing circuit. In some examples, the physiologic sensing circuit 315 is a surrogate sensor for blood pressure providing a physiologic signal that includes blood pressure information.

The control circuit 325 can include a processor such as a microprocessor, a digital signal processor, application specific integrated circuit (ASIC), or other type of processor, interpreting or executing instructions in software modules or firmware modules. In some examples, the control circuit includes a logic sequencer circuit. A logic sequencer refers to a state machine or other circuit that sequentially steps through a fixed series of steps to perform one or more functions. The steps are typically implemented in hardware or firmware. The control circuit 325 can include other circuits or sub-circuits to perform the functions described. These circuits may include software, hardware, firmware or any combination thereof. Multiple functions can be performed in one or more of the circuits or sub-circuits as desired.

The storage buffer 320 can be a memory circuit operatively coupled to or integral to the control circuit 325. In response to a detected change in posture of the subject, the control circuit 325 initiates storage of the heart rate information and the blood pressure information. In some examples, the control circuit 325 initiates collection of the heart information and the blood pressure information in response to a detected change to an upright position by the subject (e.g., when detecting a change from a supine posture to an upright posture). The heart data and blood pressure data may be collected for a specified duration of time (e.g., fifteen minutes, one or more hours, one or more days, a week, a month, etc.).

Using the stored heart rate and blood pressure information, the control circuit 325 may detect any episode of orthostatic intolerance (OI) of the subject and can generate an indication of OI in response to the detection. If the device 300 is implantable, the indication may be a signal communicated to another device that causes a presentation of the detected OI to a patient or clinician. If the device is wearable or handheld, the indication may be an alert presented using a display included with the device. In certain examples, the indication includes storing information regarding the OI in memory.

The control circuit 325 may detect orthostatic hypotension (OI) when detecting one or more of i) a change in blood pressure of the subject that is less than a specified (e.g., programmed) blood pressure threshold, ii) a change in blood pressure of the subject is greater than a specified blood pressure change threshold, or iii) detecting that the heart rate of the subject exceeds a heart rate change threshold without a corresponding change in blood pressure. The control circuit 325 may generate an indication of OH or POTS in response to the detection OI.

The time frame over which the detected changes in heart rate and blood pressure occur can also provide information useful to diagnose OI. For instance, a specified decrease in systolic blood pressure and in diastolic blood pressure that occurs within three minutes of standing may indicate Classical OH. A specified decrease in blood pressure that occurs immediately upon the subject standing and then rapidly returns to normal (e.g., within thirty seconds) may indicate Initial OH. A slow progressive decrease in systolic blood pressure that begins upon the patient assuming an upright or erect posture may indicate Delayed OH or Progressive OH. The absence of a bradycardiac reflex (vagal reflex) can differentiate Delayed OH from reflex bradycardia.

As explained previously herein, the physiologic sensing circuit 315 can be a surrogate sensor for blood pressure. In some examples, the physiologic sensing circuit 315 includes a heart sound sensing circuit that generates a sensed heart sound signal indicative of mechanical cardiac activity of the subject. The sensed heart sound signal can include information related to the S2 heart sound. The control circuit 325 initiates storage of the heart rate information and S2 heart sound information in response to the detected change in posture.

The control circuit 325 can detect OI using the S2 heart sound information. The control circuit 325 may determine OI when detecting, in association with the change in posture, one or more of i) that the amplitude of the S2 heart sound is less than a specified S2 amplitude threshold, ii) a change in amplitude of the S2 heart sound that is greater than a specified S2 heart sound amplitude change threshold, iii) detecting that heart rate of the subject exceeds a heart rate change threshold without a change in amplitude of the S2 heart sound that exceeds an S2 amplitude change threshold, or iv) that the time over with which a detected change in an S2 heart sound parameter occurs following a detected posture transition satisfies a specified threshold time. The control circuit 325 may generate an indication of orthostatic intolerance in response to the detection of OI. In some variations, S1 heart sound information is used to detect OI.

The control circuit 325 may store the heart rate information, the heart sound information, and the posture information from a detected episode of OI in association with one or more of time of day, day of a week, and activity level of the subject. For instance, a time stamp or a specified activity level can be stored with the detected information by the monitoring medical device or a remote system. Sensor data such as one or both of heart rate data and heart sound data can be parsed by storing the data according to ambulatory postural transitions detected using the posture sensor. Transitions in posture that result in episodes of OI detected by the device can be flagged in memory or can be moved to a separate area of memory. This can provide for device-based ambulatory monitoring of the patient to help in identifying any potential OI inducing triggers for the patient.

Another example of a surrogate measurement for blood pressure is pulse transit time (PTT). A physiologic sensing circuit such as an impedance sensor, a pressure sensor, or an optical sensor is located at a specified distance in the subject's body remote from the subject's heart. The physiologic sensing circuit generates a physiologic signal (e.g., an impedance signal, a pressure signal, or an optical signal) in which an arterial pulsatile shape or waveform can be detected. The cardiac signal sensing circuit 310 detects a fiducial in the cardiac signal that is representative of depolarization (e.g., a fiducial of a QRS complex). The control circuit 325 determines a time delay, or pulsatile transit time, between the sensed cardiac signal fiducial and the detection of the arterial pulse at the body location remote from the heart. This transit time provides information related to the blood pressure of the subject. In some examples, the time delay is measured from the occurrence of an S1 heart sound to the detection of the arterial pulse at the location remote from the heart.

The collection of OI-related data or information by the device 300 can be a feature enabled in the device. In some examples, the ambulatory medical device 300 is implantable and includes a communication circuit 330. The communication circuit 330 communicates wireless signals with a second separate medical device. The second device 312 can be an external communication device operated by a clinician and can include a communication circuit 335 to communicate information wirelessly with the ambulatory medical device. The collection of the heart rate information and the blood pressure information can be enabled using the second device. The control circuit 325 initiates collection of the heart information and the blood pressure information in response to a detected change to an upright position by the subject when the feature is enabled in the device. If the feature is not enabled using the second device, the OI-related information is not collected by the ambulatory device 300. In some examples, the device 300 immediately begins collecting the heart rate information and the blood pressure information in response to a signal received from the second device.

According to some examples, the device-based functions related to collecting information and detecting OI can be divided between the ambulatory medical device 300 and the second device 312. In response to the detected change in posture, the control circuit 325 can initiate communicating the heart rate information and the blood pressure information to the second device 312. The ambulatory medical device may also communicate posture information to the second device.

The second device 312 can include a processor circuit 340 that detects when the subject satisfies an OI symptomatic threshold according to the heart rate information and blood pressure information. The processor circuit 340 may detect OI when determining that the blood pressure of the subject is less than a specified blood pressure threshold, that a change in blood pressure of the subject is greater than a specified blood pressure change threshold, or that the heart rate exceeds a heart rate change threshold without a change in blood pressure that exceeds a blood pressure change threshold. The processor circuit 340 may generate an alert in response to the detecting of OI. The alert may be a visual alert presented using a display of the second medical device. The alert may be an audible alert provided using a speaker of the second device.

In some examples, the second device includes a port 345 to receive patient symptom information. The port may be a hard-wired communication port, or the port may include the communication circuit 340 and can be a wireless communication port. The processor circuit 340 may trend the heart rate information, the blood pressure information, and the posture information. For instance, changes in one or both of heart rate and heart sounds in response to a posture change (e.g., $\Delta HR = HR_{UPRIGHT} - HR_{SUPINE}$, $\Delta S2 = S2_{UPRIGHT} - S2_{SUPINE}$) can be trended. The changes can be monitored in association with detected episodes of OI. In some examples, the device 300 includes a patient activity sensor (e.g., an accelerometer incorporated into or in addition to the posture sensor) to detect syncope or inactivity related to OI.

The trended information may also be used by the processor circuit 340 to adjust an OI symptomatic detection threshold. The trended information can include one or more of the patient symptom information, heart rate information, and blood pressure information. For instance, the processor circuit 340 may change one or more of a specified blood pressure threshold, a specified blood pressure change threshold, and a specified a heart rate change threshold according to the trended information.

The trended information can be used to determine detection thresholds used to determine when an alert for the patient should be generated based on proximity of changes in heart rate and heart sounds to a history of episodes of OI. The alert can be presented by the second device if the ambulatory device is implantable, or the alert can be programmed into the ambulatory device by the second device to provide the alert if the device is wearable or handheld. Patient feedback can be incorporated into determining the symptomatic thresholds by the patient identifying OI episodes (e.g., from symptoms like dizziness) such as by using a client application (or "App") in a wearable or handheld device or by the patient tapping on the device and a vibration sensor (an accelerometer) detecting the tapping. The alert may include a syncope alert. In some examples, the alert may include diet or medication recommendations based on device-determined proximity to a symptomatic threshold of OI.

The device 300 can be used to detect other types of physiologic episodes of the patient. For instance, the device 300 may include a sensor to detect bladder evacuation by the patient. One or both of heart rate information and blood pressure information can be stored in response to detected bladder evacuation by the subject. The device may detect micturition syncope of the patient and determine symptomatic thresholds for the patient's micturition syncope.

In other examples, the device 300 can be used to detect a drop in blood pressure due to ischemia. Ischemia can be associated with an elevation in an S-wave to T-wave interval. The device may collect information related to blood pressure in response to an elevation in an S-wave to T-wave interval detected in a cardiac signal sensed using the cardiac signal sensing circuit 310.

Neutrally mediated hypotension refers to a condition where the blood pressure of the patient drops after the patient has been standing for a long period of time. The device 300 may store blood pressure information when detecting that the patient has been standing for a period of time that exceeds a specified threshold period of time.

Episodes of OI may go unreported leading to under diagnosis of OI. The episodes may not be severe enough for a patient to seek medical help. Occasional dizzy spells that may help in assessment of orthostatic response may be merely shrugged off by the patient. The systems, methods, and devices described herein can result in better detection and management of OI. OI symptoms of the patient can be monitored while the patient goes through their daily routine. This can lead to improved diagnosis and management of the patient's condition.

Additional Description and Examples

Example 1 includes subject matter (such as an ambulatory medical device system) comprising: a posture sensing circuit configured to detect a change in posture of a subject; a cardiac signal sensing circuit configured to generate a sensed cardiac signal, wherein the sensed cardiac signal includes heart rate information of the subject; a physiologic sensing circuit configured to generate a sensed physiologic signal, wherein the physiologic signal includes information related to blood pressure of the subject; a storage buffer; and a control circuit operatively coupled to the posture sensing circuit and the storage buffer and configured to store the heart rate information and the information related to blood pressure in response to a detected change in posture of the subject.

In Example 2, the subject matter of Example 1 optionally includes a control circuit configured to determine, using the stored heart rate and blood pressure information, one of that blood pressure of the subject is less than a specified blood pressure threshold, that a change in blood pressure of the subject is greater than a specified blood pressure change threshold, or that the heart rate exceeds a heart rate change threshold without a change in blood pressure that exceeds a blood pressure change threshold; and generate an indication of orthostatic intolerance in response to the detection.

In Example 3, the subject matter of one or both of Examples 1 and 2 optionally includes a physiologic sensing circuit that includes a heart sound sensing circuit that configured to generate a sensed heart sound signal indicative of mechanical cardiac activity of the subject, wherein the control circuit is configured to initiate storage of the heart rate information and S2 heart sound information as the information related to blood pressure in response to the detected change in posture.

In Example 4, the subject matter of Example 3 optionally includes a control circuit configured to determine, using the S2 heart sound information, one of that amplitude of the S2 heart sound is less than a specified S2 amplitude threshold, that a change in amplitude of the S2 heart sound is greater than a specified S2 heart sound amplitude change threshold, that the heart rate exceeds a heart rate change threshold without a change in amplitude of the S2 heart sound that exceeds an S2 amplitude change threshold, or iv) that the time over with which a detected change in an S2 heart sound parameter occurs following a detected posture transition satisfies a specified threshold time, and generates an indication of orthostatic intolerance in response to the detection.

In Example 5, the subject matter of one or both of Examples 1 and 2 optionally includes a physiologic sensing circuit that includes an implantable blood pressure sensing circuit.

In Example 6, the subject matter of one or both of Examples 1 and 2 optionally includes a physiologic sensing circuit configured to generate a physiologic signal in which an arterial pulsatile waveform is detectable at a body location remote from the heart, and wherein the control circuit is configured to store, as the information related to blood pressure, a pulsatile transmit time (PTT) determined using a fiducial detected in the sensed cardiac signal and a detected arterial pulsatile waveform.

In Example 7, the subject matter of one or any combination of Examples 1-6 optionally includes a control circuit configured to initiate the storage of the heart rate information and the information related to blood pressure in response to detecting the subject changing from a supine posture to an upright posture.

In Example 8, the subject matter of one or any combination of Examples 1-7 optionally includes a communication circuit operatively coupled to the control circuit and configured to communicate wireless signals with a second separate device, and wherein the control circuit is configured to enable the storing of the heart rate information and the information related to blood pressure in response to a signal received via the communication circuit.

In Example 9, the subject matter of one or any combination of Examples 1-7 optionally includes a communication circuit operatively coupled to the control circuit, wherein the control circuit is optionally configured to initiate communicating the heart rate information and the information related to blood pressure to a second medical device in response to the detected change in posture, and wherein the system further includes the second medical device and the second medical device includes a processor circuit configured to detect that the subject satisfies an orthostatic intolerance symptomatic threshold according to the heart rate information and the information related to blood pressure, and generate an alert in response to the detecting.

In Example 10, the subject matter of Example 9 optionally includes a second device that includes a port configured to receive patient symptom information, and wherein the processor circuit configured to trend the heart rate information, the information related to blood pressure, and the posture information and adjust one or more orthostatic intolerance symptomatic thresholds using the patient symptom information and the trended heart rate information and the information related to blood pressure.

In Example 11, the subject matter of one or both of Examples 9 and 10 optionally includes a processor circuit configured to determine one of that blood pressure of the subject is less than a specified blood pressure threshold, that a change in blood pressure of the subject is greater than a specified blood pressure change threshold, or that the heart rate exceeds a heart rate change threshold without a change in blood pressure that exceeds a blood pressure change threshold, and generate an indication of orthostatic intolerance in response to the detection.

Example 12 includes subject matter (such as an ambulatory medical device system), or can optionally be combined with the subject matter of one or any combination of Examples 1-11 to include such subject matter, comprising: a posture sensing circuit configured to detect a change in posture of a subject; a cardiac signal sensing circuit configured to generate a sensed cardiac signal, wherein the sensed cardiac signal includes heart rate information of the subject; a heart sound sensing circuit configured to generate a sensed heart sound signal, wherein the heart sound signal includes heart sound information; a storage buffer; an orthostatic intolerance detection circuit configured to detect an episode of orthostatic intolerance using the heart rate information, heart sound information, and posture information in response to detected change in posture; and a control circuit configured to store heart rate information, heart sound information, and posture information from the episode of orthostatic intolerance in association with one or more of time of day, day of a week, and activity level of the subject.

In Example 13, the subject matter of Example 12 optionally includes an orthostatic intolerance detection circuit is configured to: detect orthostatic intolerance when detecting one of that amplitude of S2 heart sound energy of the subject is less than a specified S2 amplitude threshold, that a change in amplitude of the S2 heart sound is greater than a specified S2 heart sound amplitude change threshold, or that the heart rate of the subject exceeds a heart rate change threshold and a change in amplitude of the S2 heart sound energy is less than an S2 amplitude change threshold; and generate an indication of orthostatic intolerance in response to the detection.

In Example 14, the subject matter of one or both of Examples 12 and 13 optionally includes a system including a wearable device and a second medical device, wherein the wearable device includes the posture sensing circuit, a cardiac signal sensing circuit, the heart sound sensing circuit, and a communication circuit operatively coupled to the posture sensing circuit, a cardiac signal sensing circuit, the heart sound sensing circuit, and the communication circuit is configured to communicate heart rate information, heart sound information, and posture information to the second medical device, and wherein the second medical device includes the storage buffer and the orthostatic intolerance detection circuit.

In Example 15, the subject matter of one or any combination of Examples 12-14 optionally includes a control circuit including a processor circuit configured to trend the heart rate information, the heart sound information, and the posture information, and identify one or more triggers of orthostatic intolerance using the trended information.

Example 16 includes subject matter (such as a method of operating an ambulatory medical device, a means for performing acts, or a machine-readable medium including instructions that, when performed by the machine, cause the machine to perform acts), or can optionally be combined with the subject matter of one or any combination of Examples 1-15 to include such subject matter, comprising: sensing a posture signal, wherein the posture signal includes posture information of a subject; sensing a cardiac signal, wherein the sensed cardiac signal includes heart rate information of the subject; sensing a physiological signal, wherein the sensed physiologic signal includes information related to blood pressure of the subject; detecting a change in posture of the subject using the sensed posture signal; and collecting heart rate information and the information related to blood pressure of the subject in response to the detected posture change.

In Example 17, the subject matter of Example 16 optionally includes determining, using collected heart rate information and collected information related to blood pressure, one of that blood pressure of the subject is less than a specified blood pressure threshold, that a change in blood pressure of the subject is greater than a specified blood pressure change threshold, or that the heart rate exceeds a specified heart rate change threshold while change in blood pressure is less than a specified blood pressure change threshold; and generating an indication of orthostatic intolerance in response to the detection.

In Example 18, the subject matter of one or both of Examples 16 and 17 optionally includes sensing a heart sound signal indicative of mechanical cardiac activity of the subject, and wherein the collecting heart rate information and the information related to blood pressure includes collecting the heart rate information and S2 heart sound information in response to the detected change in posture.

In Example 19, the subject matter of Example 18 optionally includes detecting orthostatic intolerance of the subject when detecting one of that amplitude of S2 heart sound energy of the subject is less than a specified S2 amplitude threshold, that a change in amplitude of the S2 heart sound is greater than a specified S2 heart sound amplitude change threshold, that the heart rate of the subject exceeds a heart rate change threshold and a change in amplitude of the S2 heart sound energy is less than an S2 amplitude change threshold, or that the time over with which a detected change in an S2 heart sound parameter occurs following a detected posture transition satisfies a specified threshold time; and generating an indication of orthostatic intolerance in response to the detection.

In Example 20, the subject matter of one or both of Examples 16 and 17 optionally includes sensing a signal representative of blood pressure of the subject using an implantable blood pressure sensing circuit.

Example 21 can include, or can optionally be combined with any portion or combination of any portions of any one or more of Examples 1-20 to include, subject matter that can include means for performing any one or more of the functions of Examples 1-20, or a machine-readable medium including instructions that, when performed by a machine, cause the machine to perform any one or more of the functions of Examples 1-20.

These non-limiting examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like. In some examples, a carrier medium can carry code implementing the methods. The term "carrier medium" can be used to represent carrier waves on which code is transmitted.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An ambulatory medical device system to monitor orthostatic intolerance of a subject, the system comprising:
   a posture sensing circuit configured to detect a change in posture of a subject;
   a cardiac signal sensing circuit configured to generate a sensed cardiac signal, wherein the sensed cardiac signal includes heart rate information of the subject;
   a heart sound sensing circuit configured to generate a sensed heart sound signal indicative of mechanical cardiac activity of the subject, the sensed heart sound signal comprising S2 heart sound information;
   a storage buffer; and
   a control circuit operatively coupled to the posture sensing circuit and the storage buffer and configured, in response to a detected change in posture of the subject, to:
      initiate storage of a portion of the heart rate information and a portion of the S2 heart sound information;
      determine, using the S2 heart sound information, a first indication that:
         amplitude of the S2 heart sound is less than a specified S2 amplitude threshold, that a change in amplitude of the S2 heart sound is greater than a specified S2 heart sound amplitude change threshold;
         the heart rate exceeds a heart rate change threshold without a change in amplitude of the S2 heart sound that exceeds an S2 amplitude change threshold; or
         the time over with which a detected change in an S2 heart sound parameter occurs following a detected posture transition satisfies a specified threshold time; and
      generate an indication of orthostatic intolerance in response to the determined first indication and the detected change in posture of the subject.

2. The system of claim 1, wherein the control circuit is configured to determine, using the stored heart rate and S2 heart sound information, one of that blood pressure of the subject is less than a specified blood pressure threshold, that a change in blood pressure of the subject is greater than a specified blood pressure change threshold, or that the heart rate exceeds a heart rate change threshold without a change in blood pressure that exceeds a blood pressure change threshold; and
   wherein the control circuit configured to generate the indication of orthostatic intolerance includes in response to the detection.

3. The system of claim 1, wherein the heart sound sensing circuit includes an implantable blood pressure sensing circuit.

4. The system of claim 1, wherein the heart sound sensing circuit is configured to generate a physiologic signal in which an arterial pulsatile waveform is detectable at a body location remote from the subject's heart wherein the control circuit is configured to store, as the information related to blood pressure, a pulsatile transmit time (PTT) determined using a fiducial detected in the sensed cardiac signal and a detected arterial pulsatile waveform.

5. The system of claim 1, wherein the control circuit is configured to initiate the storage of the heart rate information and the S2 heart sound information in response to detecting the subject changing from a supine posture to an upright posture.

6. The system of claim 1, including a communication circuit operatively coupled to the control circuit and configured to communicate wireless signals with a second separate device, and wherein the control circuit is configured to enable the storing of the heart rate information and the S2 heart sound information in response to a signal received via the communication circuit.

7. The system of claim 1, including a communication circuit operatively coupled to the control circuit,
   wherein the control circuit is configured to initiate communicating the heart rate information and the S2 heart sound information to a second medical device in response to the detected change in posture, and
   wherein the system further includes the second medical device and the second medical device includes a processor circuit configured to detect that the subject satisfies an orthostatic intolerance symptomatic threshold according to the heart rate information and the S2 heart sound information, and generate an alert in response to the detecting.

8. The system of claim 7, wherein the second device includes a port configured to receive patient symptom information, and wherein the processor circuit configured to trend the heart rate information, the S2 heart sound information, and the posture information and adjust one or more orthostatic intolerance symptomatic thresholds using the patient symptom information and the trended heart rate information and the information related to blood pressure.

9. The system of claim 7, wherein the processor circuit is configured to determine one of that blood pressure of the subject is less than a specified blood pressure threshold, that a change in blood pressure of the subject is greater than a specified blood pressure change threshold, or that the heart rate exceeds a heart rate change threshold without a change in blood pressure that exceeds a blood pressure change threshold, and generate an indication of orthostatic intolerance in response to the detection.

10. A method of controlling operation of an ambulatory medical device to detect orthostatic intolerance, the method comprising:
sensing a posture signal, wherein the posture signal includes posture information of a subject;
sensing a cardiac signal, wherein the sensed cardiac signal includes heart rate information of the subject;
sensing a heart sound signal indicative of mechanical cardiac activity of the subject, the heart sound signal comprising S2 heart sound information;
detecting a change in posture of the subject using the sensed posture signal;
initiating collection of the heart rate information and the S2 heart sound information;
determining, using the S2 heart sound information, a first indication that:
amplitude of the S2 heart sound is greater than a specified S2 heart sound amplitude change threshold, that a change in amplitude of the S2 heart sound is greater than a specified S2 heart sound amplitude change threshold;
that the heart rate of the subject exceeds a heart rate change threshold and a change in amplitude of the S2 heart sound energy is less than an S2 amplitude change threshold; or
that the time over with which a detected change in an S2 heart sound parameter occurs following a detected posture transition satisfies a specified threshold time; and
generating an indication of orthostatic intolerance in response to the determined first indication and the detected posture change.

11. The method of claim 10, including determining, using collected heart rate information and collected S2 heart sound information, one of that blood pressure of the subject is less than a specified blood pressure threshold, that a change in blood pressure of the subject is greater than a specified blood pressure change threshold, or that the heart rate exceeds a specified heart rate change threshold while change in blood pressure is less than a specified blood pressure change threshold; and
generating an indication of orthostatic intolerance in response to the detection.

12. The method of claim 10, wherein sensing the heart sound signal includes sensing a signal representative of blood pressure of the subject using an implantable blood pressure sensing circuit.

13. An ambulatory medical device system to monitor orthostatic intolerance of a subject, the system comprising:
a posture sensing circuit configured to detect a change in posture of a subject;
a cardiac signal sensing circuit configured to generate a sensed cardiac signal, wherein the sensed cardiac signal includes heart rate information of the subject;
a physiologic sensing circuit configured to generate a physiologic signal in which an arterial pulsatile waveform is detectable at a body location remote from the subject's heart, wherein the physiologic signal includes information related to blood pressure of the subject; a storage buffer; and
a control circuit operatively coupled to the posture sensing circuit and the storage buffer and configured to initiate storage of a portion of the heart rate information and a portion of the information related to blood pressure in response to a detected change in posture of the subject and to generate an indication of orthostatic intolerance using the heart rate information and the information related to blood pressure of the subject in response to the detected change in posture of the subject,
wherein the control circuit is configured to store, as the information related to blood pressure, a pulsatile transmit time (PTT) determined using a fiducial detected in the sensed cardiac signal and a detected arterial pulsatile waveform.

14. The system of claim 13, wherein the physiologic sensing circuit includes a heart sound sensing circuit configured to generate a sensed heart sound signal indicative of mechanical cardiac activity of the subject, wherein the control circuit is configured to initiate storage of S2 heart sound information as the information related to blood pressure and storage of the heart rate information in response to the detected change in posture.

15. The system of claim 14, wherein the control circuit is configured to determine, using the S2 heart sound information, one of that amplitude of the S2 heart sound is less than a specified S2 amplitude threshold, that a change in amplitude of the S2 heart sound is greater than a specified S2 heart sound amplitude change threshold, that the heart rate exceeds a heart rate change threshold without a change in amplitude of the S2 heart sound that exceeds an S2 amplitude change threshold, or that the time over with which a detected change in an S2 heart sound parameter occurs following a detected posture transition satisfies a specified threshold time, and wherein the control circuit is configured to generate the indication of orthostatic intolerance in response to the detection.

16. The system of claim 13, wherein the physiologic sensing circuit includes an implantable blood pressure sensing circuit.

17. The system of claim 13, wherein the control circuit is configured to initiate the storage of the heart rate information and the information related to blood pressure in response to detecting the subject changing from a supine posture to an upright posture.

18. The system of claim 13, including a communication circuit operatively coupled to the control circuit and configured to communicate wireless signals with a second separate device, and wherein the control circuit is configured to enable the storing of the heart rate information and the information related to blood pressure in response to a signal received via the communication circuit.

19. The system of claim 13, including a communication circuit operatively coupled to the control circuit,
wherein the control circuit is configured to initiate communicating the heart rate information and the information related to blood pressure to a second medical device in response to the detected change in posture, and
wherein the system further includes the second medical device and the second medical device includes a processor circuit configured to detect that the subject satisfies an orthostatic intolerance symptomatic threshold according to the heart rate information and the information related to blood pressure, and generate an alert in response to the detecting.

20. The system of claim 19, wherein the second device includes a port configured to receive patient symptom information, and wherein the processor circuit configured to trend the heart rate information, the information related to blood pressure, and the posture information and adjust one or more orthostatic intolerance symptomatic thresholds using the patient symptom information and the trended heart rate information and the information related to blood pressure.

* * * * *